United States Patent
Seen et al.

(10) Patent No.: US 7,528,230 B2
(45) Date of Patent: May 5, 2009

(54) ENHANCED INSERTED YELLOW FLUORESCENCE PROTEIN AND ITS APPLICATION

(75) Inventors: Dong-Seung Seen, Seoul (KR); Jac-Yong Park, Seoul (KR); Young-Shik Choi, Gyeonggi-do (KR); Eun-Wook Choi, Seoul (KR); Ho-Sun Son, Seoul (KR); Neon-C. Jung, Seoul (KR); Anthony D. Kang, Seoul (KR); Ji-Ung Maeng, Seoul (KR); Kyung-Jin Kim, Seoul (KR); Jung-Hee Shin, Seoul (KR)

(73) Assignee: Newgex, Inc., Seoul (KR)

( * ) Notice: Subject to any disclaimer, the term of this patent is extended or adjusted under 35 U.S.C. 154(b) by 367 days.

(21) Appl. No.: 10/506,925

(22) PCT Filed: Mar. 8, 2003

(86) PCT No.: PCT/KR03/00455

§ 371 (c)(1), (2), (4) Date: Sep. 7, 2004

(87) PCT Pub. No.: WO03/076466

PCT Pub. Date: Sep. 18, 2003

(65) Prior Publication Data

US 2005/0170428 A1    Aug. 4, 2005

(30) Foreign Application Priority Data

Mar. 8, 2002 (KR) .............. 10-2002-0012409
Mar. 21, 2002 (KR) .............. 10-2002-0015217
Mar. 21, 2002 (KR) .............. 10-2002-0015219

(51) Int. Cl.
*C07K 14/00* (2006.01)
*C07H 21/02* (2006.01)
*C12N 5/00* (2006.01)

(52) U.S. Cl. .................................... 530/350; 536/23.1
(58) Field of Classification Search .................... None
See application file for complete search history.

(56) References Cited

OTHER PUBLICATIONS

Genbank Accesion No. P42212.*

* cited by examiner

*Primary Examiner*—David Guzo
*Assistant Examiner*—Michele K Joike
(74) *Attorney, Agent, or Firm*—Fish & Associates, PC

(57) ABSTRACT

Disclosed are mutated genes for green fluorescence proteins and enhanced inserted YFPs expressed therefrom. The mutant proteins not only maintain their fluorescence even at 37° C., but also exhibit about 20 times stronger fluorescence intensities in comparison to the conventional fluorescence proteins. Accordingly, the mutant fluorescence proteins of the present invention can be used as biosensors for detecting and analyzing the bioactivities of desired materials.

15 Claims, 5 Drawing Sheets

FIG.3A

Time after okadaic acid (20 μM) treatment(min)

SEQUENCE LISTING

<160> NUMBER OF SEQ ID NOS: 16

<210> SEQ ID NO 1
<211> LENGTH: 738

<212> TYPE: PRT
<213> ORGANISM: Artificial Sequence
<220> FEATURE:
<223> OTHER INFORMATION: y-citrine of fluorescence protein

<400> SEQUENCE: 1

```
Ala Thr Gly Gly Thr Gly Ala Gly Cys Ala Ala Gly Gly Cys Gly
 1               5                  10                  15

Ala Gly Gly Ala Gly Cys Thr Gly Thr Cys Ala Cys Cys Gly Gly
                20                  25                  30

Gly Gly Thr Gly Gly Thr Gly Cys Cys Ala Thr Cys Cys Thr Gly
                35                  40                  45

Gly Thr Cys Gly Ala Gly Cys Thr Gly Ala Cys Gly Gly Cys Gly
         50                  55                  60

Ala Cys Gly Thr Ala Ala Cys Gly Gly Cys Cys Ala Cys Ala Ala
 65                  70                  75                  80

Gly Thr Thr Cys Ala Gly Cys Gly Thr Gly Thr Cys Cys Gly Gly Cys
             85                  90                  95

Gly Ala Gly Gly Gly Cys Gly Ala Gly Gly Gly Cys Gly Ala Thr Gly
                100                 105                 110

Cys Cys Ala Cys Cys Thr Ala Cys Gly Gly Cys Ala Ala Gly Cys Thr
            115                 120                 125

Gly Ala Cys Cys Cys Thr Gly Ala Ala Gly Thr Thr Cys Ala Thr Cys
130                 135                 140

Thr Gly Cys Ala Cys Cys Ala Cys Cys Gly Gly Cys Ala Ala Gly Cys
145                 150                 155                 160

Thr Gly Cys Cys Cys Gly Thr Gly Cys Cys Cys Thr Gly Gly Cys Cys
                165                 170                 175

Cys Ala Cys Cys Cys Thr Cys Gly Thr Gly Ala Cys Thr Ala Cys Cys
            180                 185                 190

Thr Thr Cys Gly Gly Cys Thr Ala Cys Gly Gly Cys Cys Thr Gly Ala
            195                 200                 205

Thr Gly Thr Gly Cys Thr Thr Cys Gly Cys Cys Cys Gly Cys Thr Ala
            210                 215                 220

Cys Cys Cys Cys Gly Ala Cys Cys Ala Cys Ala Thr Gly Ala Ala Gly
225                 230                 235                 240

Cys Ala Gly Cys Ala Cys Gly Ala Cys Thr Thr Cys Thr Thr Cys Ala
                245                 250                 255

Ala Gly Thr Cys Cys Gly Cys Cys Ala Thr Gly Cys Cys Cys Gly Ala
                260                 265                 270

Ala Gly Gly Cys Thr Ala Cys Gly Thr Cys Ala Gly Gly Ala Gly
                275                 280                 285

Cys Gly Cys Ala Cys Cys Ala Thr Cys Thr Thr Cys Thr Thr Cys Ala
                290                 295                 300

Ala Gly Gly Ala Cys Gly Ala Cys Gly Gly Cys Ala Ala Cys Thr Ala
305                 310                 315                 320

Cys Ala Ala Gly Ala Cys Cys Cys Gly Cys Gly Cys Cys Gly Ala Gly
                325                 330                 335

Gly Thr Gly Ala Ala Gly Thr Thr Cys Gly Ala Gly Gly Gly Cys Gly
                340                 345                 350

Ala Cys Ala Cys Cys Cys Thr Gly Gly Thr Gly Ala Ala Cys Cys Gly
            355                 360                 365

Cys Ala Thr Cys Gly Ala Gly Cys Thr Gly Ala Ala Gly Gly Gly Cys
            370                 375                 380
```

```
Ala Thr Cys Gly Ala Cys Thr Thr Cys Ala Gly Ala Gly Gly
385                 390                 395                 400

Ala Cys Gly Gly Cys Ala Ala Cys Ala Thr Cys Thr Gly Gly
                405                 410                 415

Gly Cys Ala Cys Ala Ala Gly Cys Thr Gly Gly Ala Gly Thr Ala Cys
                420                 425                 430

Ala Ala Cys Thr Ala Cys Gly Gly Thr Gly Ala Thr Cys Cys Gly
                435                 440                 445

Gly Thr Gly Cys Thr Ala Gly Cys Ala Ala Cys Ala Gly Cys Cys Ala
        450                 455                 460

Cys Ala Ala Cys Gly Thr Cys Thr Ala Thr Ala Thr Cys Ala Thr Gly
465                 470                 475                 480

Gly Cys Cys Gly Ala Cys Ala Ala Gly Cys Ala Gly Ala Ala Gly Ala
                485                 490                 495

Ala Cys Gly Gly Cys Ala Thr Cys Ala Ala Gly Gly Thr Gly Ala Ala
                500                 505                 510

Cys Th

-continued

```
  1               5              10              15
Ala Gly Gly Ala Gly Cys Thr Gly Thr Thr Cys Ala Cys Cys Gly Gly
             20                      25                      30

Gly Gly Thr Gly Gly Thr Gly Cys Cys Ala Thr Cys Cys Thr Gly
             35                      40                      45

Gly Thr Cys Gly Ala Gly Cys Thr Gly Gly Ala Cys Gly Gly Cys Gly
             50                      55                      60

Ala Cys Gly Thr Ala Ala Cys Gly Gly Cys Ala Cys Ala Ala
 65                      70                      75              80

Gly Thr Thr Cys Ala Gly Cys Gly Thr Gly Thr Cys Cys Gly Gly Cys
                     85                      90                      95

Gly Ala Gly Gly Cys Gly Ala Gly Gly Cys Gly Ala Thr Gly
             100                     105                     110

Cys Cys Ala Cys Cys Thr Ala Cys Gly Gly Cys Ala Ala Gly Cys Thr
             115                     120                     125

Gly Ala Cys Cys Cys Thr Gly Ala Ala Gly Thr Thr Cys Ala Thr Cys
             130                     135                     140

Thr Gly Cys Ala Cys Cys Ala Cys Cys Gly Gly Cys Ala Ala Gly Cys
145                     150                     155                     160

Thr Gly Cys Cys Cys Gly Thr Gly Cys Cys Thr Gly Gly Cys Cys
                     165                     170                     175

Cys Ala Cys Cys Cys Thr Cys Gly Thr Gly Ala Cys Thr Ala Cys Cys
                     180                     185                     190

Thr Thr Cys Gly Gly Cys Thr Ala Cys Gly Gly Cys Cys Thr Gly Ala
                     195                     200                     205

Thr Gly Thr Gly Cys Thr Thr Cys Gly Cys Cys Cys Gly Cys Thr Ala
                     210                     215                     220

Cys Cys Cys Cys Gly Ala Cys Cys Ala Cys Ala Thr Gly Ala Ala Gly
225                     230                     235                     240

Cys Ala Gly Cys Ala Cys G

Ala Ala Cys Thr Ala Cys Gly Gly Thr Gly Ala Thr Cys Cys Gly
        435                 440                 445

Gly Thr Gly Cys Thr Ala Gly Cys Ala Ala Cys Ala Gly Cys Ala
        450                 455                 460

Cys Ala Ala Cys Gly Thr Cys Thr Ala Thr Ala Thr Cys Ala Thr Gly
465                 470                 475                 480

Gly Cys Cys Gly Ala Cys Ala Ala Gly Cys Ala Gly Ala Ala Gly Ala
                485                 490                 495

Ala Cys Gly Gly Cys Ala Thr Cys Ala Ala Gly Gly Thr Gly Ala Ala
        500                 505                 510

Cys Thr Thr Cys Ala Ala Gly Ala Thr Cys Gly Cys Cys Ala Cys
        515                 520                 525

Ala Ala Cys Ala Thr Cys Gly Ala Gly Ala Cys Gly Gly Cys Ala
        530                 535                 540

Gly Cys Gly Thr Gly Cys Ala Gly Cys Thr Cys Gly Cys Cys Gly Ala
545                 550                 555                 560

Cys Cys Ala Cys Thr Ala Cys Cys Ala Gly Cys Ala Gly Ala Ala Cys
                565                 570                 575

Ala Cys Cys Cys Cys Ala Thr Cys Gly Gly Cys Gly Ala Cys Gly
        580                 585                 590

Gly Cys Cys Thr Cys Gly Thr Gly Cys Thr Gly Cys Thr Gly Cys Cys
        595                 600                 605

Cys Gly Ala Cys Ala Ala Cys Cys Ala Cys Thr Ala Cys Cys Thr Gly
        610                 615                 620

Ala Gly Cys Thr Ala Cys Cys Ala Gly Thr Cys Cys Gly Cys Cys Cys
625                 630                 635                 640

Thr Gly Ala Gly Cys Ala Ala Ala Gly Ala Cys Cys Cys Cys Ala Ala
645 650 655

Cys Gly Ala Gly Ala Ala Gly Cys Gly Cys Gly Ala Thr Cys Ala Cys
660 665 670

Ala Thr Gly Gly Thr Cys Cys Thr Gly Cys Thr Gly Gly Ala Gly Thr
675 680 685

Thr Cys Gly Thr Gly Ala Cys Cys Gly Cys Cys Gly Cys Cys Gly Gly
690 695 700

Gly Ala Thr Cys Ala Cys Thr Ala Thr Cys Gly Gly Cys Ala Thr Gly
705 710 715 720

Gly Ala Cys Gly Ala Gly Cys Thr Gly Thr Ala Cys Ala Ala Gly Thr
725 730 735

Ala Ala

<210> SEQ ID NO 3
<211> LENGTH: 45
<212> TYPE: DNA
<213> ORGANISM: Artificial Sequence
<220> FEATURE:
<223> OTHER INFORMATION: BamHi/5AB-F primer

<400> SEQUENCE: 3 gggggatcc gaggctggtg aggacgttgt ctgctgctcg atgtc 45

<210> SEQ ID NO 4
<211> LENGTH: 45
<212> TYPE: DNA
<213> ORGANISM: Artificial Sequence
<220> FEATURE:
<223> OTHER INFORMATION: Nhe1/5AB-R primer -continued

```
<400> SEQUENCE: 4
gggggctagc acctgtccat gtgtaggaca tcgagcagca gacaa         45

<210> SEQ ID NO 5
<211> LENGTH: 30
<212> TYPE: DNA
<213> ORGANISM: Artificial Sequence
<220> FEATURE:
<223> OTHER INFORMATION: BamHI/CaM F primer

<400> SEQUENCE: 5
gggggatcca tgcatgacca actgacagaa                          30

<210> SEQ ID NO 6
<211> LENGTH: 30
<212> TYPE: DNA
<213> ORGANISM: Artificial Sequence
<220> FEATURE:
<223> OTHER INFORMATION: NheI/CaM R primer

<400> SEQUENCE: 6
ggggctagcc tttgctgtca tcatttgtac                          30

<210> SEQ ID NO 7
<211> LENGTH: 34
<212> TYPE: DNA
<213> ORGANISM: Artificial Sequence
<220> FEATURE:
<223> OTHER INFORMATION: Hind3/EYFP(Y145MEL)-F primer

<400> SEQUENCE: 7
ggggaagctt gggatggagc tcaacagcca caac                     34

<210> SEQ ID NO 8
<211> LENGTH: 39
<212> TYPE: DNA
<213> ORGANISM: Artificial Sequence
<220> FEATURE:
<223> OTHER INFORMATION: BamHI,Nhe1/Yins-R primer

<400> SEQUENCE: 8
gttgctagca ccggatccac cgtagttgta ctccagctt                39

<210> SEQ ID NO 9
<211> LENGTH: 39
<212> TYPE: DNA
<213> ORGANISM: Artificial Sequence
<220> FEATURE:
<223> OTHER INFORMATION: BamHI,Nhe1/Yins-F primer

<400> SEQUENCE: 9
tacggtggat ccggtgctag caacagccac aacgtctat                39

<210> SEQ ID NO 10
<211> LENGTH: 33
<212> TYPE: DNA
<213> ORGANISM: Artificial Sequence
<220> FEATURE:
<223> OTHER INFORMATION: NotI/EYFP(Y145GGT)-R primer

<400> SEQUENCE: 10
gggggcggcc gcctaggtac caccgttgta ctc                      33

<210> SEQ ID NO 11
```

```
<211> LENGTH: 34
<212> TYPE: DNA
<213> ORGANISM: Artificial Sequence
<220> FEATURE:
<223> OTHER INFORMATION: Hind3/EYFP(Y145MEL)-F primer

<400> SEQUENCE: 11
ggggaagctt gggatggagc tcaacagcca caac                               34

<210> SEQ ID NO 12
<211> LENGTH: 33
<212> TYPE: DNA
<213> ORGANISM: Artificial Sequence
<220> FEATURE:
<223> OTHER INFORMATION: NotI/EYFP(Y145GGT)-R primer

<400> SEQUENCE: 12
gggggcggcc gcctaggtac caccgttgta ctc                                33

<210> SEQ ID NO 13
<211> LENGTH: 1182
<212> TYPE: DNA
<213> ORGANISM: Artificial Sequence
<220> FEATURE:
<223> OTHER INFORMATION: Bio-Cart for Calcium

<400> SEQUENCE: 13
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacta ccttcggcta cggcctgatg tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacgg tggatccatg catgaccaac tgacagaaga gcagatcgca    480
gaatttaaag aggctttctc cctatttgac aaggacgggg atgggacaat aacaaccaag    540
gagctgggga cggtgatgcg gtctctgggg cagaacccca cagaagcaga gctgcaggac    600
atgatcaatg aagtagatgc cgacggtaat ggcacaatcg acttccctga gttcctgaca    660
atgatggcaa gaaaaatgaa agacacagac agtgaagaag aaattagaga agcgttccgt    720
gtgtttgata aggatggcaa tggctacatc agtgcagcag agcttcgcca cgtgatgaca    780
aaccttggag agaagttaac agatgaagag gttgatgaaa tgatcaggga agcagacatc    840
gatggggatg gtcaggtaaa ctacgaagag tttgtacaaa tgatgacagc aaaggctagc    900
aacagccaca acgtctatat catggccgac aagcagaaga acggcatcaa ggtgaacttc    960
aagatccgcc acaacatcga ggacggcagc gtgcagctcg ccgaccacta ccagcagaac   1020
acccccatcg gcgacggccc tgtgctgctg cccgacaacc actacctgag ctaccagtcc   1080
gccctgagca agaccccaa cgagaagcgc gatcacatgg tcctgctgga gttcgtgacc   1140
gccgccggga tcactatcgg catggacgag ctgtacaagt aa                      1182

<210> SEQ ID NO 14
<211> LENGTH: 48
<212> TYPE: DNA
<213> ORGANISM: Artificial Sequence
<220> FEATURE:
<223> OTHER INFORMATION: BamHI/DEVD F primer
```

-continued

```
<400> SEQUENCE: 14 ggggatccg ccatcaagaa tgaaggaaag agaaaaggcg acgaggtg                48

<210> SEQ ID NO 15
<211> LENGTH: 49
<212> TYPE: DNA
<213> ORGANISM: Artificial Sequence
<220> FEATURE:
<223> OTHER INFORMATION: NheI/DEVD R primer

<400> SEQUENCE: 15
ggggctagcg gccacttcat ctgttccatc cacctcgtcg cctttctc                49

<210> SEQ ID NO 16
<211> LENGTH: 795
<212> TYPE: DNA
<213> ORGANISM: Artificial Sequence
<220> FEATURE:
<223> OTHER INFORMATION: DEVDins of Bio-sensor

<400> SEQUENCE: 16
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacta ccttcggcta cggcctgatg tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacgg tggatccgcc atcaagaatg aaggaaagag aaaaggcgac    480
gaggtggatg aacagatga agtggccgct agcaacagcc acaacgtcta tatcatggcc    540
gacaagcaga gaacggcat caaggtgaac ttcaagatcc gccacaacat cgaggacggc    600
agcgtgcagc tcgccgacca ctaccagcag aacaccccca tcggcgacgg cctcgtgctg    660
ctgcccgaca accactacct gagctaccag tccgccctga gcaaagaccc caacgagaag    720
cgcgatcaca tggtcctgct ggagttcgtg accgccgccg ggatcactct cggcatggac    780
gagctgtaca agtaa                                                    795
```

ENHANCED INSERTED YELLOW FLUORESCENCE PROTEIN AND ITS APPLICATION

TECHNICAL FIELD

The present invention relates to an inserted yellow fluorescence protein for defining functions of any nucleic acid sequences inserted thereto in cells. Furthermore, the present invention relates to biosensors based on the inserted yellow fluorescence proteins for detecting and analyzing bioactivities of any desired materials.

BACKGROUND

Green fluorescence protein (hereinafter, referred to as "GFP") was originally isolated from a jellyfish. Since GFP protein consists of a number of 238 amino acids, and since it does not need any other proteins or substrates for fluorescence activation, it has been widely used as a reporter protein. Various types of GFP mutants have been reported. EGFP (enhanced GFP) was prepared by increasing intensity of GFP's fluorescence; and BFP (blue fluorescence protein), CFP (cyan fluorescence protein) and YFP (yellow fluorescence protein) were prepared by modifying fluorescence spectrum.

In 1998, it was firstly reported that fluorescence intensity of GFP was maintained even after inserting foreign protein or a part of protein or peptides thereto at one or more sites (see NAR 26:623-630). Since then, molecules belonging to the group of the inserted fluorescence proteins, which were developed by R Tsien et al., have been used. YFPins and Camgaroo, which was made by inserting calmodulin to the YFPins, were representative inserted fluorescence proteins designed by R Tsien et al. (see PNAS 96:11241-11246). The mutant fluorescence proteins, however, did not show fluorescence activities at 37° C., while they displayed fluorescence activities at 28° C. Thus, they could not be used as biosensors in mammalian cell to measure activities of any desired materials. R Tsien et al. also reported that Camgaroo 2 (Q69M mutant), which was made by substituting 69th amino acid sequence of Glutamine with Methionin, represented fluorescence even at 37° C. However, the fluorescence intensity of the Camgaroo 2 was so weak that it could not be used in the measurement of calcium at a single cell level. Accordingly, there has been the need to find a novel inserted fluorescence protein having even stronger fluorescence.

Concerning viral disease, since the cause of disease was not defined clearly in general the obtaining of molecules, which inhibit activities of the disease-causing enzymes, has been the primary subject for the drug development these days. In this regard, an efficient cell-based assay system to monitor activities of target proteins of viral disease was required. Particularly, regarding human Hepatitis C virus, which cannot be cultivated in a laboratory, the development of a useful cell-based pharmacological assay system to define drug efficacy in a cell was greatly required. Although NS3 protease or NS5B RNA polymerase has been considered as an important target protein for the development of drug for the treatment of viral disease of human Hepatitis C, there has not been any efficient cell-based assay system to determine the effects of drug. Until now, recombinant viruses designed to have lifecycle dependent on NS3 protease activity have been used as cell-based reporting systems for detecting the activity of NS3 protease. Jang, seung-gi reported in 1996 an assay system using NS3 protease dependent poliovirus (see Virology 226: 318-26), and Jecyca et al. reported in 1998 other assay system using Sindbis virus for detecting NS3 protease activity (J. Virol 73:561-575). In addition, other assay system using BVDV (bovine viral diarrhea virus) was disclosed in a published document in 2000 (see J. Virol 74: 6339-6347). These assay systems for detecting and analyzing NS3 protease's activity using viruses belonging to Flaviviridae family, which had similar molecular biological features, were proved to have useful features. However, these systems had several problems to be resolved as high through put assay systems. These systems regarded to use original viruses as controls, and viral infection problem arose after the cell culture, in the procedures of detecting inhibitors. Therefore, the demand for more efficient and more cost effective assay system is still very high.

It is known that caspase recognizes and cleavages a protein at the site of amino acids following aspartic acid. In 1998, Xu et al. detected caspase-3 (CPP32) activity using FRET (Fluorescence Resonance Energy Transfer) that was caused by placing DEVD (SEQ ID No.: 17) amino acid sequence between GFP and BFP (see NAR 26:2034-2035). Also, BD bioscience clontech designed a system to monitor the activity of caspase-3 through tracing and investigating the YEP within a cell by fusing DEVD-YEP and nuclear export sequence (BD bioscience clontech, PR1Z499W). However, in detecting caspase activity using FRET, signal/noise (S/N) ratio was too low for practical application in the assay system. In addition, this assay system, which was basically based on protein movement in a cell, required relatively expensive device, and it was difficult to digitize the enzyme activity since the detected results were secondary signals. Accordingly, there have been great needs to find more efficient and cost effective cell-based assay system to detect and analyze the activities of materials.

Thus, in order to provide biosensors for studying activities of numerous desired materials in cells, we carried out researches to develop new type of inserted fluorescence proteins maintaining appropriate fluorescence intensities around 37° C., and thereby we designed enhanced inserted yellow fluorescence proteins by inducing mutations to the inserted fluorescence proteins. Then, we designed a new type of biosensor for detecting activity of NS3 protein inhibitor of human Hepatitis C virus by inserting the NS3 protein inhibitor's substrate recognition sites into the enhanced inserted fluorescence protein. Also, we designed a new type of calcium sensor for determining the amount of calcium in a cell by inserting calmodulin recognition sites into the prepared enhanced inserted fluorescence protein. Furthermore, we developed a new type of caspase sensor to detect caspase activity in a cell by inserting caspase recognition site into the obtained enhanced inserted fluorescence protein.

DETAILED DESCRIPTIONS OF THE INVENTION

Any publications referenced herein are hereby incorporated by reference in this application in order to more fully describe the state of the art to which the present invention pertains.

It is important to understand the present invention to note that all technical and scientific terms used herein, unless otherwise defined, are intended to have the same meaning as commonly understood by one of ordinary skill in the art. The techniques used herein are also well-known to any one with ordinary skill in the art, unless stated otherwise.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of suggested method, material or composition is directed.

It is an object of the present invention to provide an inserted yellow fluorescence protein having enhanced fluorescence intensity at 37° C.

It is another object of the present invention to provide a biosensor to understand various life phenomena in cells.

In order to accomplish these objects, mutations are induced in conventional inserted fluorescence.

Specifically, $145^{th}$ amino acid of Tyrosine, which is deleted in the conventional inserted fluorescence protein, is introduced. In addition, pcDNA3 (Invitrogen #V79020) vector is prepared, wherein 2 (two) restriction enzyme (BamHI and NheI) recognition sites are placed for efficient cloning of numerous insertion regions. Then, PCR cloning is carried out with the vector to induce mutations. The resultant mutant fluorescence protein maintains intensive fluorescence.

Thus, the obtained and selected mutant inserted yellow fluorescence protein, according to the above method, is characterized by including "YGGSGAS" (partial sequence of SEQ ID No.:1) at 145th amino acid site, wherein the amino acid site is insertion region of foreign protein or a part of protein. This mutant inserted fluorescence protein is named as Y-Citrine (SEQ.ID No.: 1). The insertion region is designed to function as a binding site that has little electricity in comparison to that of the conventional inserted fluorescence protein. Since the insertion region has restriction enzyme recognition sites, which cannot be found in conventional vectors, it is possible to clone numerous genes into the vector with just one cloning process.

Furthermore, a novel mutant inserted yellow fluorescence protein named as Peridot (SEQ.ID No.: 2), which has additional mutation of replacement of 192nd amino acid of Proline with Leucine (P192L), is provided.

These 2 (two) mutation inserted yellow fluorescence proteins showed about 20 times stronger fluorescence than the conventional inserted fluorescence proteins, under confocal microscopes (see FIG. 1).

Furthermore, biosensors for detecting bioactivities of any materials and for monitoring activities of protease are provided with the Peridot. For example, a sensor for assaying NS3 protein inhibitor of human Hepatitis C virus, a calcium sensor and a Caspase sensor are designed.

With regard to the sensor for detecting and analyzing NS3 protein inhibitor of human Hepatitis C virus, it is provided by inserting amino acid sequences encoding inhibitor's substrate recognition sites into the insertion region of the two developed inserted fluorescence proteins. Specifically, primers of BamHI/5AB-F'-GGGGGGATCC GAGGCTGGTG AGGACGTTGT CTGCTGCTCG ATGTC-3' (SEQ. ID No.: 3) and NheI/5AB-R 5'-GGGGGCTAGC ACCTGTCCAT GTGTAGGACA TCGAGCAGCA GACAA-3' (SEQ. ID No.: 4), which encode substrate recognition sites for the NS3 protease, are synthesized and combined, and then are cloned with restriction enzymes. In order to confirm the maintenance and the intensity of fluorescence of the substrate sensor, it is introduced into HeLa cell line and examined and investigated under confocal microscope (see FIG. 1). If the substrate biosensor prepared above maintains its fluorescence within a cell, it must be a useful cell-based substrate biosensor for detecting the activity of foreign NS3 protease.

Furthermore, in order for a biosensor binding calcium in a cell to be provided, calmodulin gene, which binds calcium, is introduced into BamHI and/or NheI restriction enzyme recognition sites in Peridot. More specifically, PCR is carried out using calmodulin gene, as a template, and BamHI/CaM F primer 5'-GGGGGATCCATGCATGACCAACTGACA-GAA-3' (SEQ. ID No.: 5) and NheI/CaM R primer 5'-GGGGCTAGCCTTTGC TGTCATCATTTGTAC-3' (SEQ. ID No.: 6). Next, gene cloning is carried out at BamHI and NheI recognition sites with BamHI and NheI recognition enzymes, and the resulting recombinant gene is named as BCC (bio-cart for calcium). Subsequently, the prepared BCC is transferred to HeLa cell line (ATCC# CCL-2) and is incubated for at least 24 hrs at 37° C. After the incubation, the HeLa cell line having the BCC is examined under confocal microscope to monitor the change of fluorescence while radiating it with Argon laser (480 nm). Specifically, while monitoring the fluorescence, the HeLa cell line is continuously treated with 10 M of cabacol, 1 M of calcium ionopore, 100 mM of calcium solution and calcium-free solution (see FIG. 2).

FIG. 2A shows photographic images captured at 5-second intervals. FIG. 2B illustrates time-dependent graphic images showing changes of calcium for the 4 (four) cells disclosed in FIG. 2A. Although each of the 4 (four) cells show different fluorescence intensities dependent on the level of inserted BCC genes, it is observed that all the cells responded in similar ways to external stimuli. It can be clarified by normalizing the fluorescence intensities with the fluorescence intensities detected before imposing the stimuli. FIG. 2C shows the normalized graphic images, which strongly support that BCC is a efficient cell-based calcium sensor exactly representing the calcium in cells.

Furthermore, a caspase sensor is provided using Peridot to monitor the activity of caspase in a cell. For this purpose, DEVD (SEQ ID No.: 17) amino acid sequence is inserted into the Peridot, and it is named DEVDins. The produced DEVDins is transferred to CHO-K1 (Chinese hamster ovarian) cell line, and then DEVDins expressing cell line is selected and named as CHO-K1-DEVDins. After that, the selected cell line is treated with cell death inducing agent, and the activity of caspase-2/3/7 is detected using quantitative fluorescence image analysis (see FIG. 3). Thus, recombinant fluorescence proteins including caspase recognition amino acid sequences, are provided.

BRIEF DESCRIPTIONS OF FIGURES

In FIG. 1A, A) is for Citrine-Ins, B) is for Y-Citrine, C) is for Peridot, D) is for Y-Citrine-5AB and E) is for Peridot-5AB.

FIG. 2B illustrates quantified graphic images of photographs of FIG. 2A under confocal microscope.

Figure 3A:
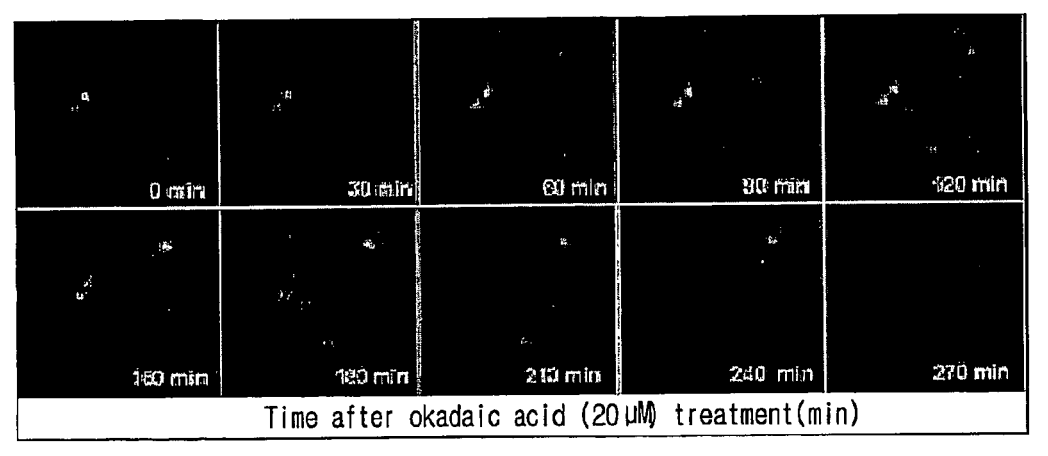

FIG. 3A is fluorescence photographs taken after treating HeLa cell lines, which have caspase sensors, with cell death inducing agent of okadaic acid (20 mM/ml).

Preferred embodiments of this invention are described in the following examples. Other embodiments within the scope of the claims herein will be apparent to those skilled in the art from consideration of the specification or practice of the invention as disclosed herein. It is intended that the specification, together with the examples, be considered exemplary only, with the scope and the spirit of the invention being indicated by the claims that follow the example. The examples herein are meant to exemplify the various aspects of carrying out the invention and not intended to limit the scope of the invention in any way. The examples do not include detailed descriptions of conventional methods employed, such as in the performance of genomic DNA isolation, PCR, and sequencing procedures. Such methods are well known to those skilled in the art and are described in numerous publications. In addition, all the publications referred herein are integrated hereto as references.

EXAMPLES

Example 1

Determination of Fluorescence Intensities of Inserted Fluorescence Proteins

Figure 1A:
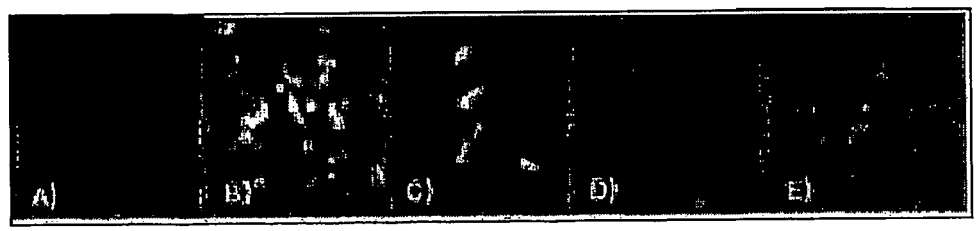
FIG. 1A is fluorescence photographs of HeLa cell lines captured by confocal microscope after introducing the inserted fluorescence proteins of the present invention and substrate biosensor for NS3 protease of human Hepatitis C virus.
Figure 1B:
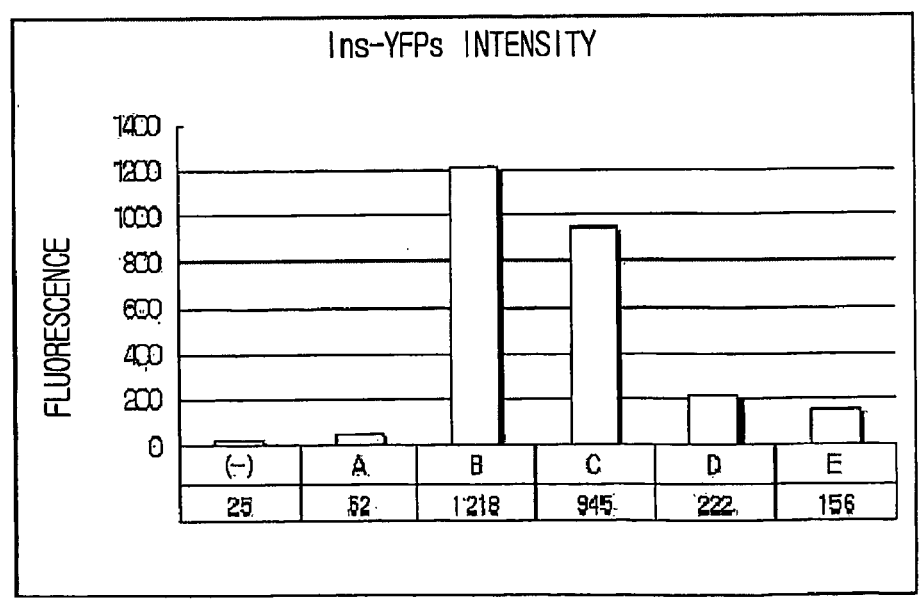
FIG. 1B illustrates graphic images representing relative quantified fluorescence intensities of the inserted fluorescence proteins of the present invention.

In order to obtain a mutant inserted fluorescence protein having enhanced fluorescence intensity at 37° C., $145^{th}$ amino acid of Tyrosine, which was deleted in the conventional fluorescence protein, was introduced into the conventional inserted yellow fluorescence protein. On the other hand, 2 (two) restriction enzyme recognition sites (HindIII and NotI) were introduced into pcDNA3 vector, which was designed to express genomic materials in mammalian cells, for gene cloning. For this purpose, 4 (four) primers were used. PCR amplification for 5' region was carried out using YFP (Clontech #6006-1), as a template, and a pair of primers of Hind3/EYFP (Y145MEL)-F 5'-GGGGAAGCTT GGGATGGAGC TCAACAGCCA CAAC-3' primer (SEQ. ID No.: 7) and BamHI,NheI/Yins-R 5'-GTT GCT AGC ACC GGA TCC ACC GTA GTT GTA CTC CAG CTT-3' (SEQ. ID No.: 8). In addition, PCR amplification for 3' region was carried out using YFP (Clontech #6006-1), as a template, and a pair of primers of BamHI, NheI/Yins-F 5'-TAC GGT GGA TCC GGT GCT AGC AAC AGC CAC AAC GTC TAT-3' (SEQ. ID No.: 9) and NotI/EYFP(Y145GGT)-R 5'-GGGGGCGGCC GCCTAGGTAC CACCGTTGTA CTC-3' (SEQ. ID No.: 10). And then, additional PCR amplification was carried out using the above PCR products, as templates, and a pair of primers, Hind3/EYFP(Y145MEL)-F 5'-GGGGAAGCTT GGGATGGAGC TCAACAGCCA CAAC-3' (SEQ. ID No.: 11) and NotI/EYFP(Y145GGT)-R 5'-GGGGGCGGCC GCCTAGGTAC CACCGTTGTA CTC-3' (SEQ. ID No.: 12). Following the application, the resultant mutants were cloned to pcDNA3 vector using Hid3 and NotI restriction enzymes. The prepared mutants were transferred to HeLa cell lines, and the mutants which maintained the fluorescence at 37° C. were selected therefrom. In FIG. 1A, A) shows fluoresce photography of Citrine-Ins, which was prepared by R Tsien et al., under the confocal microscope.

Since the sensitivity of confocal microscope is very low, the fluorescence intensity, which can be detected under the general fluorescent microscope, cannot be detected under the confocal microscope. Thus, the photography of FIG. 1A had black background. The inserted fluorescence proteins of the present invention, such as B) Y-Citrine and C) Peridot as shown in FIG. 1A, represented about 20 times stronger intensities than the conventional fluorescence proteins.

Example 2

Preparation of a Substrate Biosensor for NS3 Protease of Human Hepatitis C Virus Using Inserted Fluorescence Protein In order to develop a substrate biosensor for determining the activity of NS3 protease inhibitor, amino acid sequences encoding the NS3 protease's substrate recognition site were introduced into the insertion region of the inserted yellow fluorescence protein. The NS3 protease inhibitor of human Hepatitis C virus recognizes protein-binding sites, such as NS34A, 4A4B, 4B5A and 5A5B, as substrate recognition sites. Particularly, since the 5A5B binding site has excellent feature as substrate, it has been used in protease activity assay system using similar viruses. Therefore, NS5A5B (or 5AB) was used as substrate recognition site in this example also. In order to insert this substrate recognition site into the protein insertion region of the inserted fluorescence protein, primers of BamHi/5AB-F 5'-GGGGGGATCC GAGGCTGGTG AGGACGTTGT CTGCTGCTCG ATGTC-3' (SEQ. ID No.: 3) and Nhe1/5AB-R 5'-GGGGGCTAGC ACCTGTCCAT GTGTAGGACA TCGAGCAGCA GACAA-3' (SEQ. ID No.: 4) were synthesized and combined within a tube, and then were subject to cloning with recognition enzymes of BamHI and NheI. Next, the prepared biosensor was transferred to HeLa cell line and examined under the confocal microscope in order to measure fluorescence and its intensity. In FIG. 1A, D) shows a fluorescence photography of Y-Citrine-5AB including substrate recognition site within the inserted fluorescence protein Y-Citrine, and E) shows a fluorescence photography of Peridot-5AB including substrate recognition sites within inserted fluorescence protein of Peridot. Although the fluorescence intensities of these sensors were lower than those of the inserted fluorescence proteins not having insertion, they generated significantly enhanced fluorescence intensities in comparison to that of inserted fluorescence protein of R Tsien et al., Citrin-Ins.

Thus, the prepared substrate sensors for NS3 protein inhibitor maintained the fluorescence intensities in cells, and they should be considered as being useful substrate sensors for detecting NS3 protease activities.

Example 3

Preparation of a Calcium Sensor Using Inserted Fluorescence Protein

Figure 2A:
FIG. 2A is photographs of HeLa cell lines captured at 5-second intervals while continuously treating the cell lines, which include calcium sensor BCC with 10 M of cabacol, 1 M of calcium ionopore, 100 mM of calsuim solution and calcium-free solution.
Figure 2C:
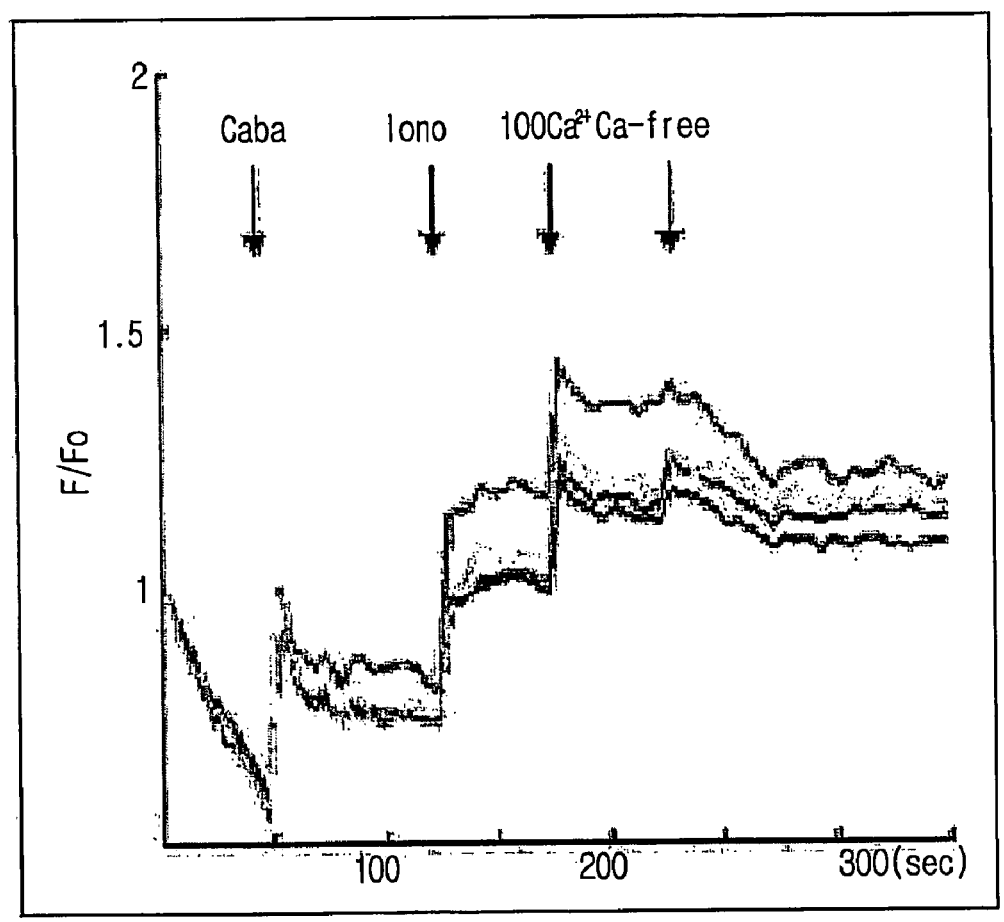
FIG. 2C illustrates normalized graphs of the graphs of FIG. 2B using fluorescence intensities before applying stimulus.
Figure 3B:
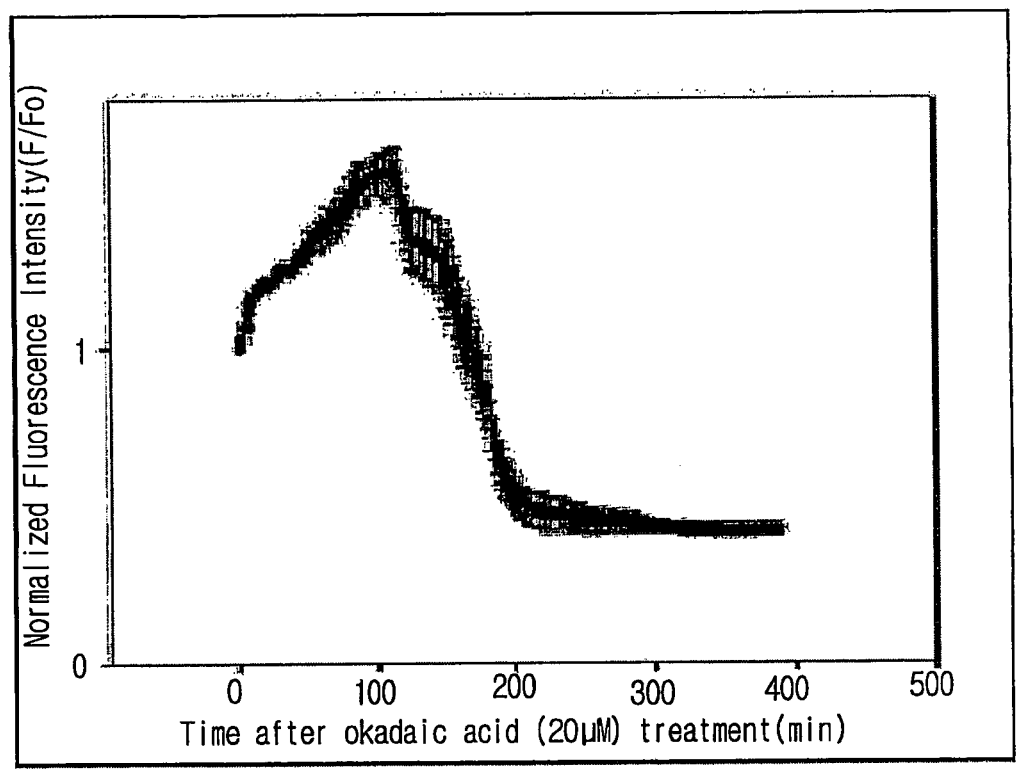
FIG. 3B illustrates quantified graphs of the photographs of FIG. 3A.

A calcium sensor, which binds calcium in cells, was provided in this example. First, calmodulin gene was transferred to BamHI and NheI recognition sites to prepare the calcium sensor. In order to insert calmodulin into the inserted fluorescence protein, a pair of primers of BamHI/CaM F 5'-GGGG-GATCCATGCATGACCAACTGACAGAA-3' (SEQ. ID No.: 5) and NheI/CaM R 5'-GGGGCTAGCCTTTGC TGT-CATCATTTGTAC-3' (SEQ. ID No.: 6) were synthesized. Then, PCR was carried out using calmodulin cDNA, as template, and the primers. Subsequently, amplified PCR products were cloned to peridot insertion region with restriction enzymes of BamHI and NheI, and the resultant recombinant gene was named as BCC (Bio-Cart for Calcium) (SEQ. ID No.: 13). Next, the produced BCC was transferred to HeLa cell line, and the fluorescence intensity of BCC within the cell line was examined with Argon Laser (480 nm) under confocal microscope. Considering that the BCC has calmodulin domain at cylinder type loop construct of YFP, it was thought that the structural modification caused by the binding between calmodulin and calcium might result in the change of fluorescence intensity. While determining the fluorescence intensity of the HeLa cell line including BCC, the cell line was treated with 10 M of cabacol, 1 M of calcium ionopore, 100 mM of calcium solution and calcium-free solution continuously. FIG. 2A shows images captured at 5-second intervals, and FIG. 2B illustrates graphic images representing time-dependent change of calcium for the 4 (four) cells that were disclosed in FIG. 2A. Each of the 4 cells responded to the foreign stimuli in similar ways, although the fluorescence intensities were somewhat different from each other based on the level of insertion of BCC genes. It is clarified in FIG. 2C that illustrates graphic images, which are normalized with fluorescence intensities obtained before imposing the stimuli. The enhanced fluorescence intensities, which were induced by the change of calcium amount, were maintained for some time period. Thus, it was confirmed that BCC could be used as a cell-based sensor indicating the amount of calcium in a cell, wherein the amount of calcium changed sensitively to the external stimuli.

Considering the fact that, with the conventional high through-put assay system, it usually takes about 3 minutes to monitor every hole of 96-hole plate, the BCC can be considered as being an excellent biosensor that can be used in various experiments to detect and analyze calcium, since it maintains its fluorescence intensity 5 min or more to the same external stimuli.

Example 4

Preparation of a Caspase Sensor Using Inserted Fluorescence Protein

A caspase sensor, which can be used in monitoring the activity of caspase, was prepared in this example using inserted fluorescence protein. DEVD amino acid sequences (SEQ ID No.: 17, which were recognized by caspase 2/3/7, were introduced into insertion region of the inserted fluorescence protein so that the fluorescence intensity of prepared biosensor can be in direct proportion to the change of the activities of caspase. With the prepared biosensor, it was possible to detect activity of caspase 2/3/7 under fluorescent microscope and was possible to digitize the activities. As mentioned in the example 1, a pair of primers of BamHI/ DEVD F 5'-GGGGGATCCGCCATCAAGAATGAAG-GAAAG AGAAAAGGCGACGAGGTG-3' (SEQ. ID No.: 14) and NheIIDEVDR 5'-GGGGCTAGCG GCCACTTCAT CTGTTCCATC CACCTCGTCG CCTTTTCTC-3' (SEQ.ID No.: 15) were synthesized and then were combined. Next, the combined primers were cloned into the insertion region in peridot with restriction enzyme, and the resultant product was named DEVDins (SEQ. ID No.: 16). After transferring the DEVDins to CHO-K1(Chinese hamster ovarian, ATCC #CCL61) cell line, the cell line was treated with cell death inducing agent in order to activate caspase to monitor the fluorescence intensity. As a result, it was observed that the fluorescence intensity of the prepared biosensor decreased due to the denaturation of the inserted fluorescence protein by the activated caspase.

INDUSTRIAL APPLICABILITY

The present invention provides novel inserted yellow fluorescence proteins generating about 20 times stronger fluorescence intensity in mammalian cells (at 37° C.) in comparison to those of conventional proteins of the same kind. Therefore, with the present enhanced inserted yellow fluorescence proteins, it is possible to carry out cell-based studies for numerous materials.

Insertion of protein-binding site of NS5AB, which is known as a substrate recognition site of NS3 protease of human Hepatitis C virus, provides a substrate biosensor for NS3 protease. Thus, it is possible to develop HCV protease assay system, which can be used in monitoring any desired materials in cells, using the inserted fluorescence proteins, such as Y-Citrine-5AB and Peridot-5AB, as substrates. Accordingly, those skilled in the art can design protease activity assay system by preparing sensor cell line firstly using the substrate sensor and by introducing NS3 gene of human Hepatitis C virus into the cell line. Furthermore, it is obvious for those skilled in the art to design cell-based activity assay biosensor by inserting substrate recognition site of foreign protein, for example, originating from virus.

Development of a biosensor of the present invention, which can quantify the amount of calcium in cells in real-time, provides essential ways to carry out real-time studies for, such as, cell death, epilepsy and neurosis etc. In addition, with the biosensor, it is possible to develop pharmacological assay system for numerous diseases accompanying the change in the amount of calcium.

Furthermore, the development of caspase sensor of the present invention, which can detect protease activity in cells in real-time, makes it possible to design anti-cancer drug assay system. Likewise, this kind of sensor can be used in numerous disease assay systems by employing various disease-associated proteases.

The substantial feature of the biosensors based on the inserted yellow fluorescence proteins is that these biosensors can be used to detect and to analyze any desired materials in cells in real-time. This unique feature of the biosensors of the present invention provides advantages in deciding suitable time point for assay and in conducting assays repeatedly, in carrying out pharmacological assays. Furthermore, additional costs for quantification are not required in using these biosensors. Thus, in accordance with the present invention, cost effective high through put pharmacological assay is possible with the enhanced inserted yellow fluorescence proteins.

What is claimed is:

1. An enhanced inserted yellow fluorescence protein according to SEQ ID NO: 1, wherein the amino acid sequence of YGGSGAS beginning at position 146 enhances fluorescence of the protein as compared to the inserted yellow fluorescence protein without the amino acid sequence of YGGSGAS.

2. A nucleic acid sequence encoding the enhanced inserted yellow fluorescence protein as claimed in claim 1.

3. The nucleic acid sequence as claimed in claim 2 comprising BamHI and NheI restriction enzyme recognition sites.

4. The enhanced inserted yellow fluorescence protein as claimed in claim 1, wherein the 199$^{th}$ amino acid (proline) in SEQ ID NO:1 is replaced by leucine to form a modified enhanced inserted yellow fluorescence protein having a sequence according to SEQ ID NO:2.

5. A nucleic acid sequence encoding the enhanced inserted yellow fluorescence protein as claimed in claim 4.

6. The enhanced inserted yellow fluorescence protein as claimed in claim 1 or claim 4 further comprising an additional peptide covalently coupled to the enhanced inserted yellow fluorescence protein.

7. A nucleic acid sequences encoding the enhanced inserted yellow fluorescence protein as claimed in claim 6.

8. The enhanced inserted yellow fluorescence protein as claimed in claim 6, the additional peptide comprising an NS3 protease's substrate recognition site of human Hepatitis C virus (HCV NS3).

9. A nucleic acid sequence encoding the enhanced inserted yellow fluorescence protein as claimed in claim 8.

10. The enhanced inserted yellow fluorescence protein as claimed in claim 6, wherein the additional peptide has a sequence that allows the additional peptide to bind calcium.

11. A nucleic acid sequence encoding the enhanced inserted yellow fluorescence protein as claimed in claim 10.

12. The enhanced inserted yellow fluorescence protein as claimed in claim 6, the additional peptide comprising a DEVD amino acid sequence (SEQ ID NO:17) recognizable by caspase.

13. A nucleic acid sequence encoding the enhanced inserted yellow fluorescence protein as claimed in claim 12.

14. A bioactivity assay system, for use in vivo or in vitro, comprising the enhanced inserted yellow fluorescence protein as claimed in claim 6.

15. A biosensor, for use in vivo or in vitro, comprising the enhanced inserted yellow fluorescence protein as claimed in claim 1 or claim 4.

* * * * *

UNITED STATES PATENT AND TRADEMARK OFFICE
CERTIFICATE OF CORRECTION

PATENT NO. : 7,528,230 B2  Page 1 of 1
APPLICATION NO. : 10/506925
DATED : May 5, 2009
INVENTOR(S) : Dong-Seung Seen et al.

It is certified that error appears in the above-identified patent and that said Letters Patent is hereby corrected as shown below:

On title page, item 75 Inventors,
replace "Jac-Yong Park"
with "Jae-Yong Park."

Signed and Sealed this

Eleventh Day of May, 2010

David J. Kappos
*Director of the United States Patent and Trademark Office*